US012782283B2

(12) United States Patent
Maeda et al.

(10) Patent No.: US 12,782,283 B2
(45) Date of Patent: Nov. 3, 2026

(54) METHOD FOR DETECTING TYROSINE RESIDUE IN SAMPLE, AND TERBIUM COMPOUND TO BE USED FOR SUCH DETECTION

(71) Applicant: NEC CORPORATION, Tokyo (JP)

(72) Inventors: Katsumi Maeda, Tokyo (JP); Masayoshi Tsuji, Tokyo (JP)

(73) Assignee: NEC CORPORATION, Tokyo (JP)

( * ) Notice: Subject to any disclaimer, the term of this patent is extended or adjusted under 35 U.S.C. 154(b) by 941 days.

(21) Appl. No.: 18/071,076

(22) Filed: Nov. 29, 2022

(65) Prior Publication Data

US 2023/0168196 A1 Jun. 1, 2023

(30) Foreign Application Priority Data

Nov. 30, 2021 (JP) ................................ 2021-194970

(51) Int. Cl.

*G01N 21/00* (2006.01)
*G01N 21/64* (2006.01)
*G01N 33/533* (2006.01)
*G01N 33/58* (2006.01)
*C09K 11/77* (2006.01)

(52) U.S. Cl.

CPC ....... *G01N 21/6428* (2013.01); *G01N 33/533* (2013.01); *G01N 33/582* (2013.01); *A23V 2250/0652* (2013.01); *C03C 2201/3458* (2013.01); *C09K 11/7743* (2013.01)

(58) Field of Classification Search

CPC ................................................ G01N 21/6428
USPC ........................................................ 436/86
See application file for complete search history.

(56) References Cited

FOREIGN PATENT DOCUMENTS

| | | | |
|---|---|---|---|
| JP | 2001-517796 | A | 10/2001 |
| JP | 2008-504528 | A | 2/2008 |
| JP | 2010-006713 | A | 1/2010 |
| WO | 2019/053964 | A1 | 3/2019 |

OTHER PUBLICATIONS

Moussa et al. "Importance of Hydrogen-Bonding Sites in the ChiralRecognition Mechanism Between Racemic D3Terbium(III) Complexes and Amino Acids" CHIRALITY 21:497-506 (2009) (Year: 2009).*
Kenjiro Hanaoka "Fluorescent labeling reagent", Drug Delivery System, 2017, pp. 425-429, 32-5.
Japanese Office Action for JP Application No. 2022-189823, mailed on Sep. 1, 2026 with English Translation.
A Moussa et al., Importance of hydrogen-bonding sites in the chiral recognition mechanism between racemic D3 terbium3complexes and amino acids, 20090531, vol. 21, No. 5, 497-506, DOI: 10.1002/chir.20628.

* cited by examiner

*Primary Examiner* — Lyle Alexander
*Assistant Examiner* — Emily R. Berkeley
(74) *Attorney, Agent, or Firm* — Sughrue Mion, PLLC

(57) ABSTRACT

An example objective of the present invention is to provide a method for detecting a tyrosine residue in a sample and a compound that can be used in the method. One aspect of the present embodiment relates to a method for detecting a tyrosine residue in a sample, wherein fluorescence emission from a reaction product of a terbium compound represented by the predetermined formula and a tyrosine residue is detected.

6 Claims, 6 Drawing Sheets

METHOD FOR DETECTING TYROSINE RESIDUE IN SAMPLE, AND TERBIUM COMPOUND TO BE USED FOR SUCH DETECTION

This application is based upon and claims the benefit of priority from Japanese patent application No. 2021-194970, filed on Nov. 30, 2021, the disclosure of which is incorporated herein in its entirety by reference.

TECHNICAL FIELD

The present invention relates to a method for detecting a tyrosine residue in a sample, a fluorescence-labeling reagent for detecting a tyrosine residue and a terbium compound to be used for such detection. The present invention relates to a sensor for detecting a tyrosine residue.

BACKGROUND ART

Fluorescence labeling of a site of specific structure in a polypeptide, a biological matrix, or a virus with a fluorescence-labeling reagent allows visualization or detection of the presence or reaction behavior of the site of specific structure, and hence various fluorescence-labeling reagents have been developed. Specifically, fluorescence-labeling reagents for amino ($—NH_2$) group and thiol (—SH) group in amino acids, which are structural units of proteins, have been already put into practical use. For example, Non Patent Document 1 describes a fluorescent dye having isothiocyanate group, succinimidyl ester group, or the like as a reagent for selectively fluorescence-labeling amino group, and describes a fluorescent dye having maleimide group or iodomaleimide group as a reagent for selectively fluorescence-labeling thiol group.

Patent Document 1 discloses a method for fluorescence detection of phosphorylated tyrosine by using a terbium complex of specific structure.

CITATION LIST

Patent Literature

Patent Document 1: Japanese Patent Laid-Open No. 2001-517796

Non Patent Literature

Non Patent Document 1: Fluorescent labeling reagent, Kenjiro Hanaoka, Drug Delivery System 32-5, 2017, p.425-429.

SUMMARY OF INVENTION

Technical Problem

However, a reagent capable of fluorescence labeling of nonphosphorylated tyrosine residues has not been developed yet.

An object of the present embodiment is to provide a method for detecting a tyrosine residue in a sample, and a compound applicable to the same.

Solution to Problem

One aspect of the present embodiment relates to a method for detecting a tyrosine residue in a sample, wherein fluorescence emission from a reaction product of a terbium compound and a tyrosine residue is detected, the terbium compound being represented by the following formula (1):

(1)

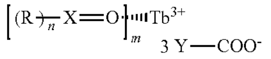

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same X atom or different X atoms are optionally attached to each other; X represents phosphorus atom or sulfur atom; Y represents hydrocarbon group having 1 to 12 carbon atoms; n represents an integer of 1 to 3 and m represents an integer of 0 to 5; and, if m is 2 or more, X atoms may be identical to or different from each other.

Advantageous Effect of Invention

According to one aspect of the present embodiment, a method for detecting a tyrosine residue in a sample can be provided. According to one aspect of the present embodiment, a compound to be used to detect a tyrosine residue in a sample can be provided.

DESCRIPTION OF EMBODIMENTS

Figure 1:
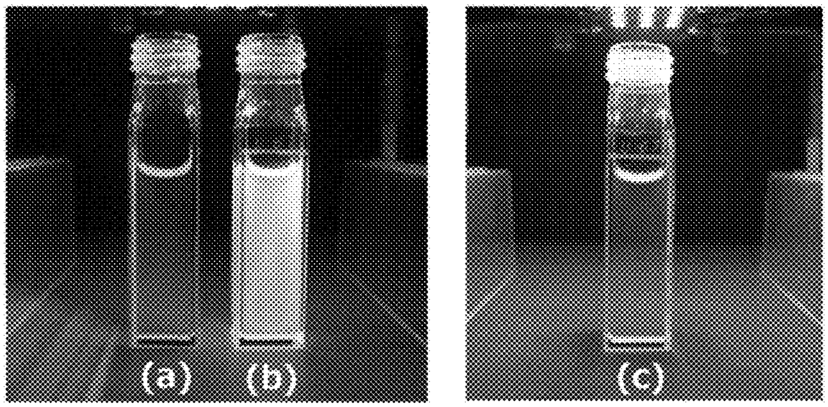
FIG. 1 shows photographs for confirming fluorescence emission in Example 1, wherein (a) shows a result for a DMSO solution of terbium pivalate (TbPv), (b) shows a result for a DMSO solution of TbPv+N-acetyl-L-tyrosine ethyl ester monohydrate (Ac-Tyr-OEt), and (c) shows a result for a DMSO solution of Ac-Tyr-OEt.

The present inventors diligently studied to solve the problem described above. The results led to a finding that compounds having a tyrosine residue can be detected by using a terbium compound of specific structure, and eventually the present invention was made.

Hereinafter, while embodiments according to the present invention will be described, they are not intended to limit the present embodiment to those described below. As used herein, the phrase of "selectively detects a tyrosine residue" means that the tyrosine residue can be specifically detected. Specifically, in a measurement of fluorescence intensity at a specific wavelength, the fluorescence intensity emitted by reacting a terbium compound with a tyrosine residue is significantly greater than the fluorescence intensity of a reaction product obtained by reacting the terbium compound with other major amino acid residues (such as phenylalanine, serine, tryptophan, arginine, asparagine, histidine, or the like), and thereby allowing detection of the tyrosine residues. For example, in the measurement of fluorescence intensity at a specific wavelength, the fluorescence intensity of the reaction product obtained by reacting a terbium compound with a tyrosine residue is preferably 5 times or more, more preferably 10 times or more, and further more preferably 20 times or more greater than that of a reaction product (or mixture) of the terbium compound with a compound including an amino acid that does not have a tyrosine residue.

One aspect of the present embodiment relates to a method for (preferably selectively) detecting a tyrosine residue in a sample, wherein fluorescence emission from a reaction product of a terbium compound and a tyrosine residue is detected, the terbium compound being represented by the following formula (1):

$$\left[(R)_{n}X{=}O\right]_{m}\cdots Tb^{3+}\quad 3\,Y{-}COO^{-} \qquad (1)$$

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same X atom or different X atoms are optionally attached to each other; X represents phosphorus atom or sulfur atom; Y represents hydrocarbon group having 1 to 12 carbon atoms; n represents an integer of 1 to 3 and m represents an integer of 0 to 5; and, if m is 2 or more, X atoms may be identical to or different from each other.

In the detection method of the present embodiment, fluoresce emitted from a terbium complex formed through reaction of a tyrosine residue and a specific terbium compound is detected. This detection method allows selective detection of a tyrosine residue in a sample (such as a matrix) containing amino acids, a peptide, a virus, or the like, measurement of the concentration thereof, and visualization of the reaction behavior of a tyrosine residue and others. Use of the terbium compound of the present embodiment enables selective detection of fluorescence even for nonphosphorylated tyrosine residues. Accordingly, a simpler fluorescence detection method can be provided, without need of advance phosphorylation of tyrosine residues as in known techniques.

In the present embodiment, a "tyrosine residue" refers to a divalent group given by removing one hydroxy group from the carboxyl group attached to the a-carbon of tyrosine and removing one hydrogen from the amino group attached to the same a-carbon. Each tyrosine residue may be either in the L-form or in the D-form, and the L-form is preferred in one aspect. Herein, a tyrosine residue is occasionally expressed as a "tyrosine structure".

Examples of the compound having a tyrosine residue include the amino acid tyrosine or derivatives thereof, and peptides or derivatives thereof. Such tyrosine derivatives may be, for example, those with tyrosine whose amino group and/or carboxyl group has been modified, and examples thereof include tyrosine whose amino group has been acetylated.

Peptide is a compound having a structure in which multiple amino acids are linked via amide bonds. Examples of the peptide include oligopeptide having a structure in which 2 to 10 amino acids are linked via amide bonds (such as dipeptide, tripeptide, tetrapeptide, pentapeptide, hexapeptide, heptapeptide, octapeptide), and polypeptide (protein) having a structure in which 11 or more amino acids are linked via amide bonds. Each peptide may be modified at the N terminus and/or C terminus.

In the present embodiment, the "sample" is not limited, and examples thereof include those containing amino acids, a peptide, a biological matrix, a virus, or a compound or the like. If a compound in the sample contains a tyrosine residue, a complex is formed through reaction with the terbium compound of the present embodiment.

<Terbium Compound>

In the present embodiment, a terbium compound represented by the formula (1) below (occasionally referred to as "terbium compound", simply) is used for detection of a tyrosine residue:

$$\left[(R)_{n}X{=}O\right]_{m}\cdots Tb^{3+}\quad 3\,Y{-}COO^{-} \qquad (1)$$

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same X atom or different X atoms are optionally attached to each other; X represents phosphorus atom or sulfur atom; Y represents hydrocarbon group having 1 to 12 carbon atoms; n represents an integer of 1 to 3 and m represents an integer of 0 to 5; and, if m is 2 or more, X atoms may be identical to or different from each other.

In the formula (1), R groups each independently represent alkyl group having 1 to 8 carbon atoms, alkenyl group having 2 to 8 carbon atoms, cycloalkyl group having 3 to 8 carbon atoms, or substituted or unsubstituted aryl group. The alkyl group having 1 to 8 carbon atoms may be linear or branched, and examples thereof include methyl group, ethyl group, propyl group, isopropyl group, n-butyl group, tert-butyl group, pentyl group, hexyl group, heptyl group, and octyl group. Examples of the alkenyl group having 2 to 8 carbon atoms include vinyl group, 2-propenyl group (allyl group), 3-butenyl group, 1-methylvinyl group, 2-methylvinyl group, 1-methylpropenyl group, and 2-methylpropenyl group. Examples of the cycloalkyl group having 3 to 8 carbon atoms include cyclopropyl group, cyclobutyl group, cyclopentyl group, and cyclohexyl group. Examples of the substituted or unsubstituted aryl group include phenyl group, methoxyphenyl group, dimethylaminophenyl group, thienyl group, furanyl group, and pyridyl group. If a plurality of R groups is present, they may be identical to or different from each other, preferably being identical in one aspect. A plurality of (preferably two) R groups attached to the same X atom may be attached to each other, and they may form a ring. R groups attached to different X atoms may be attached to each other, and they may form a ring.

In the formula (1), Y represents hydrocarbon group having 1 to 12 carbon atoms. Y is preferably alkyl group having 1 to 12 carbon atoms (preferably having 1 to 8 carbon atoms), cycloalkyl group having 3 to 12 carbon atoms, or aryl group. Examples of the alkyl group having 1 to 12 carbon atoms include methyl group, ethyl group, propyl group, isopropyl group, n-butyl group, tert-butyl group, pentyl group, hexyl group, heptyl group, octyl group, nonyl group, decanyl group, undecanyl group, and dodecanyl group. Examples of the cycloalkyl group having 3 to 12 carbon atoms include cyclopropyl group, cyclobutyl group, cyclopentyl group, and cyclohexyl group. Examples of the aryl group include phenyl group.

Examples of the counteranion (Y—$COO^-$) in the formula (1) include carboxylate ion such as acetate ion, propanoate ion, pivalate ion, isobutyrate ion, cyclohexanecarboxylate ion, cyclopentanecarboxylate ion, and benzoate ion.

In the formula (1), n is an integer of 1 to 3. In one aspect, n=3 is preferred if X is phosphorus atom, and n=2 is preferred if X is sulfur atom.

In the formula (1), m represents an integer of 0 to 5, and is preferably an integer of 0 to 3. If m is 2 or more, X atoms may be identical to or different from each other, and are preferably identical.

In one aspect of the present embodiment, the terbium compound is preferably a compound represented by the following formula (2):

(2)

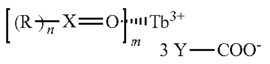

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same X atom or different X atoms are optionally attached to each other; X represents phosphorus atom or sulfur atom; Y represents hydrocarbon group having 1 to 12 carbon atoms; n represents an integer of 1 to 3 and m represents an integer of 1 to 5; and, if m is 2 or more, X atoms are identical to or different from each other.

The explanation of the formula (1) applies to R, X, Y and n in the formula (2). In the formula (2), m represents an integer from 1 to 5, and is preferably an integer from 1 to 3. When m is 2 or more, a plurality of X may be identical to or different from each other.

In one aspect of the present embodiment, the terbium compound is preferably a compound represented by the following formula (3).

(3)

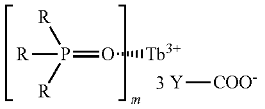

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same P atom or different P atoms are optionally attached to each other; Y represents hydrocarbon group having 1 to 12 carbon atoms; and m represents an integer of 1 to 5.

The explanation of the formula (1) applies to R and Y in the formula (3). In the formula (3), m represents an integer from 1 to 5, and is preferably an integer from 1 to 3.

In one aspect of the present embodiment, the terbium compound is preferably a compound represented by the following formula (4).

(4)

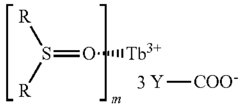

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same S atom or different S atoms are optionally attached to each other; Y represents hydrocarbon group having 1 to 12 carbon atoms; and m represents an integer of 1 to 5.

The explanation of the formula (1) applies to R and Y in the formula (4). In the formula (4), m represents an integer from 1 to 5, and is preferably an integer from 1 to 3.

Specific examples of the terbium compound include, but are not limited to, terbium salts such as terbium acetate, terbium pivalate, terbium propionate, terbium isobutyrate, terbium cyclopentanecarboxylate, terbium benzoate, terbium nonanoate, terbium valerate, and the like; complexes of the terbium salt and a phosphine oxide derivative as shown in Table 1; and complexes of the terbium salt and a sulfoxide derivative as shown in Table 2.

TABLE 1

| | Structural Formula |
|---|---|
| TbPv-NBPO | 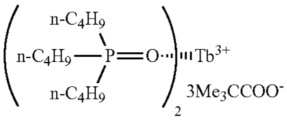 |
| TbPv-CH3PO | 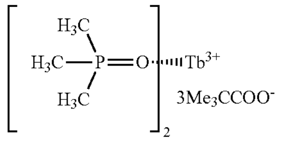 |

TABLE 1-continued
| | Structural Formula |
|---|---|
| TbA-MTPO | 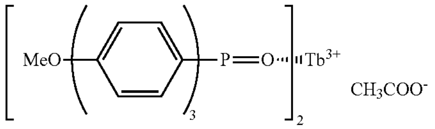 |
| TbPv-NOPO | 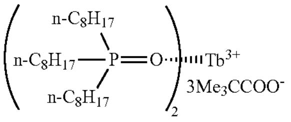 |
| TbA-TTPO | 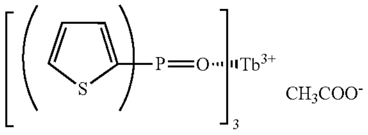 |
| TbA-BDPO | 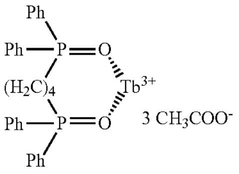 |
| TbPv-NBPO-3 | 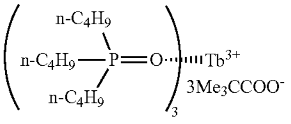 |
| TbA-NOPO | 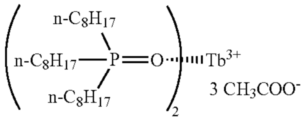 |
| TbPv-NBPO-1 | 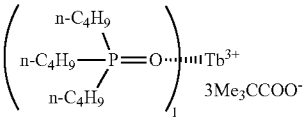 |
| TbA-tBPO | 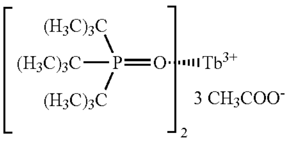 |
| TbA-PDPO | 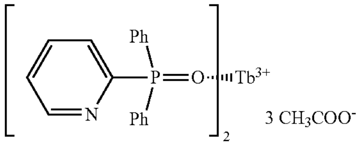 |
| TbPv-NOPO | 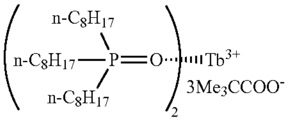 |
TABLE 2
| | Structural Formula |
|---|---|
| Tb-1 | 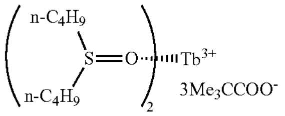 |
| Tb-2 | 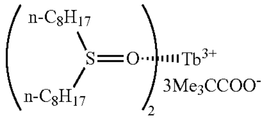 |
| Tb-3 | 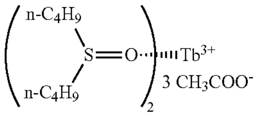 |
| Tb-4 | 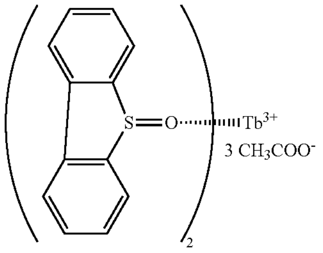 |
| Tb-5 | 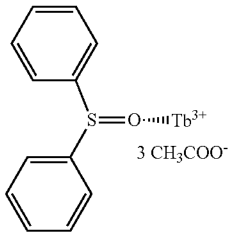 |
| Tb-6 | 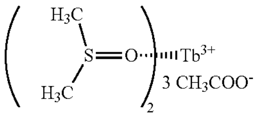 |
| Tb-7 | 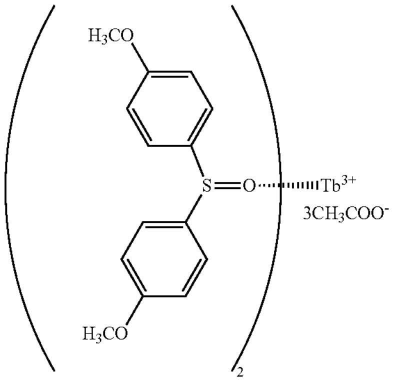 |
| Tb-8 | 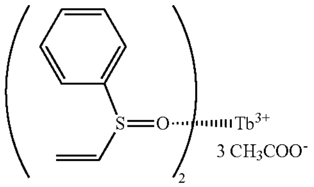 |

TABLE 2-continued

| | Structural Formula |
|---|---|
| Tb-9 | 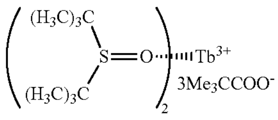 |
| Tb-10 | 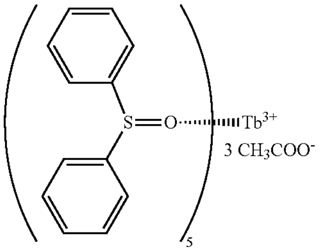 |
| Tb-11 | 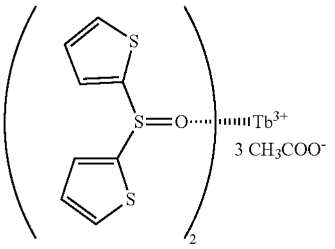 |
| Tb-12 | 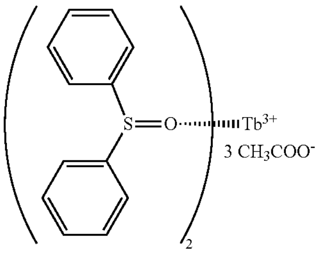 |
| Tb-13 | 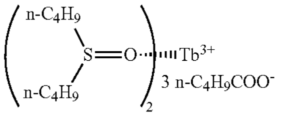 |

<Method for Producing Terbium Compound>

Among terbium compounds represented by the formula (1), a compound (terbium salt) with mn=0 can be synthesized by reacting terbium chloride hexahydrate and sodium carboxylate in water as shown in the reaction formula (11) below. Y in the formula (11) have the same meaning as Y defined for the formula (1).

Formula (11)

$$TbCl_3 \cdot 6H_2O + 3\ Y\text{—}COONa \xrightarrow[-3NaCl]{} Tb(Y\text{—}COO)_3$$

Terbium pivalate (TbPv) can be synthesized, for example, by reacting terbium chloride hexahydrate and sodium pivalate in water as shown in the following formula (11-1).

Formula (11-1)

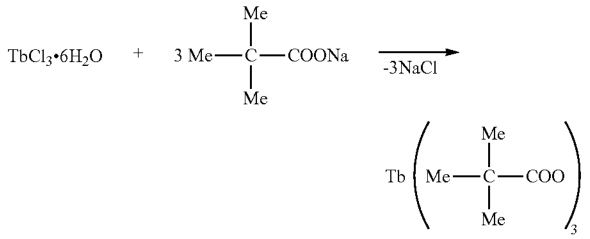

Among terbium compounds represented by the formula (1), a compound with m being 1 or more (i.e., a terbium compound represented by the formula (2)) can be synthesized by reacting a terbium salt obtained through the above reaction formula (11) and a phosphine oxide derivative or sulfoxide derivative in ethanol or methanol with heating as shown in the reaction formula (12) below. R, X, Y, m, and n in the formula (12) have the same meanings as R, X, Y, m, and n in the formula (2).

Formula (12)

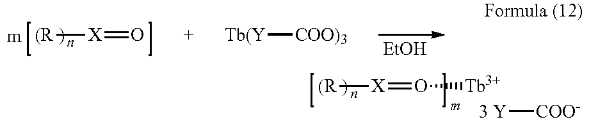

A complex of terbium pivalate and tri-n-butylphosphine oxide (TbPv-NBPO) can be synthesized, for example, by reacting terbium pivalate and tri-n-butylphosphine oxide in ethanol with heating as shown in the following formula (12-1).

Formula (12-1)

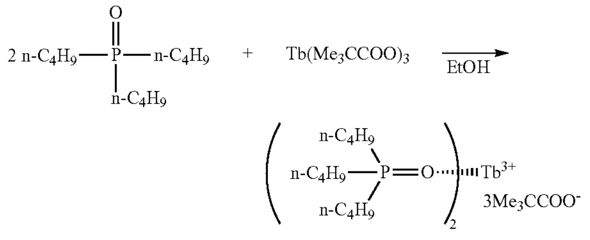

In the present embodiment, fluorescence emitted from a terbium complex of formed through reaction of a compound (such as a matrix) having a tyrosine residue and the above terbium compound is detected. The terbium compound of the present embodiment reacts with a tyrosine residue as follows. For example, terbium pivalate reacts with a tyrosine derivative (e.g., N-acetyl-L-tyrosine ethyl ester) as shown in a formula (13) below, thus being capable of (preferably selectively) recognizing tyrosine structures. A terbium complex formed through the interaction is excited by ultraviolet light to exhibit fluorescence emission characteristic to the terbium compound, and the intensity is significantly higher than that in the absence of the tyrosine derivative; thus, detecting this allows visualization of the presence of a tyrosine structure.

Formula (13)

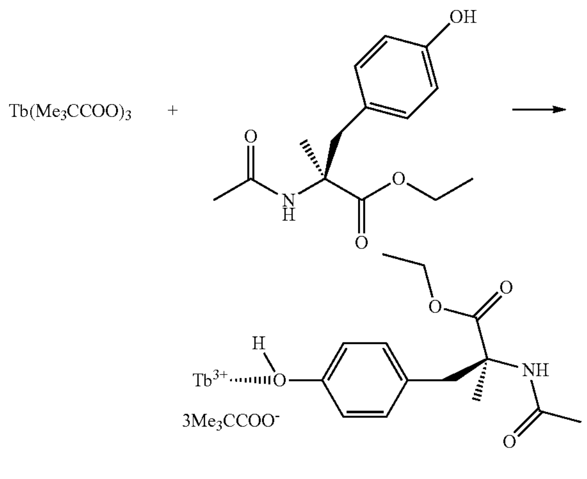

<Phenomenon of Fluorescence Emission>

The complex generated through the reaction of the terbium compound represented by the formula (1) and a tyrosine residue (tyrosine structure) newly exhibits fluorescence emission. Specifically, the complex formed through the reaction of the terbium compound and a tyrosine residue exhibits fluorescence emission on being irradiated preferably with excitation light having a wavelength of 200 to 400 nm, more preferably with excitation light having a wavelength of 280 to 330 nm. On the other hand, the terbium compound alone exhibits almost no fluorescence emission. Accordingly, such fluorescence emission allows detection of tyrosine structures. In one aspect of the present embodiment, the concentration of tyrosine residues in a sample (matrix) is determined by comparing the intensity of detected fluorescence with a predetermined reference value.

In one aspect of the present embodiment, the reaction of the terbium compound and a sample (such as a matrix) is performed in a solution. Examples of the solvent (excluding an ionic liquid) that may be used to dissolve the terbium compound include dimethyl sulfoxide, an alcohol such as methanol and ethanol, water, N,N-dimethylformamide, tetrahydrofuran, acetone, acetonitrile, 1,4-dioxane and the like, but are not limited to these solvents. An ionic liquid described below may also be used in place of or in addition to the solvent(s). In one aspect of the present embodiment, for example, the concentration of the terbium compound represented by the formula (1) in the reaction solution is preferably in the range of 0.00001 mol/L to 5 mol/L, and more preferably in the range of 0.00004 mol/L to 1 mol/L.

In one aspect of the present embodiment, the reaction of the terbium compound and a sample (such as a matrix) is performed in a solid medium containing the terbium compound. The solid medium can be, for example, paper (e.g., filter paper), glass (e.g., a glass fiber, a porous glass substrate), or resin (e.g., polymethyl methacrylate, polyethylene, polypropylene, polyvinyl chloride, polystyrene, nylon resin, polyamide, polycarbonate, polyethylene terephthalate, polybutylene terephthalate, polyphenylene oxide) or water-soluble polymer (such as cellulose-based polymer, agarose, starch-based polymer, sodium arginate, acrylate-based polymer, acrylamide-based polymer, polyvinyl alcohol, polyethylene oxide, polyvinylpyrrolidone), but is not limited thereto.

In one embodiment of the present invention, an ionic liquid described below may be used for the reaction of the terbium compound and a sample (matrix, etc.). For example, when a paper is used as a medium, the terbium compound is dissolved in a solvent (e.g., the above solvent to dissolve the terbium compound) and the ionic liquid is added to the resultant. Then, the resulting solution is permeated into a paper (e.g., a filter paper) and dried at from room temperature to 60° C. to remove the solvent. Consequently, the medium containing the terbium compound and the ionic liquid is obtained. The medium may be permeated with a mixture of the terbium compound and a non-volatile ionic liquid without using the solvent. However, the use of the solvent is preferred because it facilitates permeation of the terbium compound into the medium and adjusting the concentration of the terbium compound. After the solvent is removed, the terbium compound may be dissolved in the non-volatile ionic liquid, or may be partly precipitated in some cases. The terbium compound can detect a tyrosine residue whether it is dissolved in a non-volatile ionic liquid or precipitated.

The ratio of the ionic liquid to the solvent may be appropriately set for the medium to be permeated. If the ratio of the ionic liquid to the solvent is too small, the amount of the ionic liquid in the medium after drying may be small, and thus the effect of improving the detection sensitivity may be reduced in some cases. On the other hand, if the ratio of the ionic liquid to the solvent is too large, there may be a disadvantage of making it difficult to permeate the ionic liquid into the medium due to the high viscosity of the ionic liquid. Therefore, the ratio of the ionic liquid to the solvent may be appropriately set for the medium. For example, when a filter paper is permeated, the ratio of the ionic liquid to the solvent is preferably 5 to 50% by weight, more preferably 10 to 30% by weight.

One aspect of the present embodiment relates to a fluorescence-labeling reagent for (preferably selectively) detecting a tyrosine residue, wherein the fluorescence-labeling reagent (also simply described as "reagent") contains a terbium compound represented by the formula (1).

Herein, the term "reagent" is defined as a chemical substance used for detection or quantification of a substance by chemical methods, synthesis experiment or measurement of a physical property of a substance.

In one aspect of the present embodiment, the fluorescence-labeling reagent may further comprise an ionic liquid. Inclusion of the ionic liquid in the fluorescence-labeling reagent improves the detection sensitivity of a tyrosine residue.

(Ionic Liquid)

The ionic liquid that may be used in the present embodiment is preferably a non-volatile ionic liquid. Examples of the ionic liquid include an imidazolium salt, a phosphonium salt, a pyridinium salt, an ammonium salt, a piperidinium salt, a pyrrolidinium salt and the like. Specifically, examples thereof include, but are not limited to, 1-ethyl-3-methylimidazolium acetate, 1-butyl-3-methylimidazolium acetate, 1-ethyl-3-methylimidazolium tetrafluoroborate, 1-butyl-1-methylpyrrolidinium bis(fluorosulfonyl)imide, 1-butylpyridinium bis(trifluoromethanesulfonyl)imide, 1-methyl-1-propylpiperidinium bis(fluorosulfonyl)imide, 1-ethyl-3-methylimidazolium bis(trifluoromethanesulfonyl)imide, 1-butyl-3-methylimidazolium dicyanamide and the like.

The weight ratio of the ionic liquid to the terbium compound is not particularly limited, but is preferably 2 to 40 times, more preferably 3 to 30 times, and particularly preferably 4 to 20 times. If the weight ratio of the ionic liquid to the terbium compound is too small, the effect of improving the detection sensitivity of a tyrosine residue may not be obtained in some cases. If the weight ratio of the ionic liquid to the terbium compound is too large, it may be difficult for the terbium compound to form a complex with a tyrosine residue in some cases.

The reagent for detecting a tyrosine residue of the present embodiment may optionally comprise other solvents as long as the effects of the present invention are not impaired. Examples of the other solvents that may be used include, but are not limited to, dimethylsulfoxide, methanol, ethanol, water, N,N-dimethylformamide, tetrahydrofuran, acetone, acetonitrile, 1,4-dioxane, and the like.

In the method for detecting a tyrosine residue of the present embodiment, the above fluorescence-labeling reagent may be used, and the reagent may be reacted with a sample to obtain a reaction product.

One aspect of the present embodiment relates to a method for (preferably selectively) detecting a tyrosine residue in a sample, the method including the steps of.

(i) reacting a terbium compound represented by the formula (1) and a sample to obtain a reaction product;
(ii) irradiating the resulting reaction product with excitation light; and
(iii) detecting excited fluorescence.

In one aspect, a proper wavelength in the range of 200 to 400 nm (more preferably 280 to 330 nm) is selected as the excitation wavelength. In one aspect, a step of determining the concentration of tyrosine structures in a matrix by comparing the intensity of detected fluorescence with a predetermined reference value may be further performed.

One aspect of the present embodiment relates to a method for detecting a matrix having a tyrosine structure, the method including the steps of:

(i) reacting a terbium compound represented by the formula (1) and a matrix having a tyrosine structure to form a complex;
(ii) irradiating the complex with excitation light; and
(iii) detecting fluorescence emitted from the complex.

In one aspect of the present embodiment, a proper wavelength in the range of 200 to 400 nm (more preferably 280 to 330 nm) is selected as the excitation wavelength. In one aspect, a step of determining the concentration of tyrosine structures in a matrix by comparing the intensity of detected fluorescence with a predetermined reference value can be further performed.

One aspect of the present embodiment relates to a sensing method for allowing a tyrosine structure in a sample to be (preferably selectively) recognized by using a terbium compound represented by the above formula (1).

One aspect of the present embodiment relates to a method for sensing a matrix having a tyrosine structure, wherein fluorescence emitted from a complex of terbium formed through reaction of a tyrosine structure and a terbium compound represented by the above formula (1) is detected. In this sensing method, the above fluorescence-labeling reagent may be used.

One aspect of the present embodiment relates to a sensor for (preferably selectively) detecting a matrix having a tyrosine structure, the sensor at least including a detection section configured to detect fluorescence emission from a reaction product of a terbium compound represented by the formula (1) and a tyrosine residue. The sensor may further comprise a recognition section that comprises the terbium compound represented by formula (1) and recognizes the tyrosine structure, and the recognition section may comprise the above fluorescence-labeling reagent. The detection section detects that a tyrosine structure is recognized by the recognition section.

One aspect of the present embodiment relates to a sensor for (preferably selectively) detecting a tyrosine structure, the sensor at least including a detection section configured to detect fluorescence emission from a reaction product of a terbium compound represented by the formula (1) and a tyrosine residue. In one aspect, the detection section at least includes an excitation light source (light emission section) and a detecting element (light reception section for fluorescence). In one aspect, the sensor of the present embodiment allows detection of and/or concentration measurement for tyrosine structures on the basis of change in fluorescence intensity observed.

The detection section in the sensor for (preferably selectively) detecting a tyrosine structure may comprise a computer that executes a program for handling detection of and/or concentration measurement for tyrosine structures. Such a program may be, for example, a program that commands a computer to execute a step of receiving a signal from the optical detection element, a step of determining the presence or absence of a tyrosine structure and/or the concentration thereof by analyzing the received signal, and a step of outputting an analysis result. In some embodiments, the analysis of a received signal may include, for example, determining the presence or absence of a tyrosine structure and/or the concentration thereof in a matrix by comparing a received signal with a predetermined reference value. In some embodiments, the analysis result may be outputted, for example, on a display connected to the sensor, or on other equipment or the like connected via a network.

Accordingly, some embodiments of the present invention relate to a sensor for (preferably selectively) detecting a tyrosine structure, the sensor at least comprising a detection section that detects fluorescence emission from a reaction product of a terbium compound represented by the formula (1) and a tyrosine residue, wherein the detection section comprises a detecting element and a computer and has a program that commands a computer to execute (i) a step of receiving a signal from the optical detection element, (ii) a step of determining the presence or absence of a tyrosine structure and/or the concentration thereof by analyzing the received signal, and (iii) a step of outputting an analysis result.

EXAMPLES

Hereinafter, the present invention will be described in more detail with reference to specific examples; however, the present invention is not limited thereto.

Synthesis Example 1

<Synthesis of Terbium Pivalate>

In 30 mL of water, 2 g of terbium chloride hexahydrate was dissolved, to which 2.284 g of sodium pivalate dissolved in water was added, and the resultant was stirred at room temperature. Terbium pivalate precipitated was separated through filtration, washed with water, and then dried under reduced pressure to obtain 2.09 g of the target product.

Synthesis Examples 2 to 5

Different terbium compounds (right column in Table 3) were obtained in the same manner as in Synthesis Example 1, except that sodium carboxylates listed in Table 3 were used in place of sodium pivalate.

TABLE 3

| Synthesis Example | Sodium carboxylate | Terbium compound |
|---|---|---|
| 1 | sodium pivalate | terbium pivalate |
| 2 | sodium isobutyrate | terbium isobutyrate |
| 3 | sodium cyclohexanecarboxylate | terbium cyclohexanecarboxylate |
| 4 | sodium cyclopentanecarboxylate | terbium cyclopentanecarboxylate |
| 5 | sodium nonanoate | terbium nonanoate |

Synthesis Example 6

<Synthesis of Complex of Terbium Pivalate and Tri-n-Butylphosphine Oxide (TbPv-NBPO)>

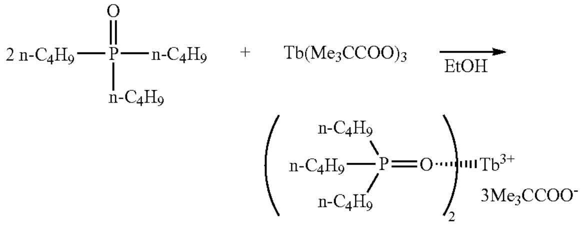

In 30 mL of ethanol, 0.3 g of terbium pivalate obtained in Synthesis Example 1 and 0.409 g of tri-n-butylphosphine oxide were dissolved, and the resultant was heated to reflux for 4 hours. After allowing to cool, ethanol was distilled off under reduced pressure, 30 mL of diethyl ether was added to the residue, unreacted terbium pivalate precipitated was removed through filtration, and the filtrate was concentrated and dried under reduced pressure to obtain 0.677 g of the target complex of terbium pivalate and tri-n-butylphosphine oxide. The characteristic absorption of P═O in the FTIR spectrum for the complex obtained was at 1131 $cm^{-1}$. On the other hand, the characteristic absorption of P═O in the FTIR spectrum for the raw material tri-n-butylphosphine oxide was at 1154 $cm^{-1}$, which indicated a shift of the characteristic absorption of P═O to the low frequency side, thus demonstrating the coordinate bond of tri-n-butylphosphine oxide to the terbium ion.

Synthesis Examples 7 to 9

Complexes of any one of different terbium compounds and phosphine oxide were obtained in the same manner as in Synthesis Example 6, except that terbium compounds (terbium salts) and phosphine oxide derivatives listed in Table 4 were used in place of terbium pivalate and tri-n-butylphosphine oxide.

TABLE 4

| Synthesis Example | terbium compound | Phosphine oxide derivative | Complex of terbium compound and phosphine oxide | P═O characteristic absorption ($cm^{-1}$) |
|---|---|---|---|---|
| 6 | terbium pivalate | tri-n-butylphosphine oxide | TbPv-NBPO | 1131 |
| 7 | terbium pivalate | trimethylphosphine oxide | TbPv-$CH_3$PO | 1134 |
| 8 | terbium pivalate | tri-n-octylphosphine oxide | TbPv-NOPO | 1134 |
| 9 | terbium acetate | tri-n-octylphosphine oxide | TbA-NOPO | 1136 |

Synthesis Example 10

<Synthesis of Complex of Terbium Pivalate and Tri-n-Butylphosphine Oxide (TbPv-NBPO-1)>

Synthesis was performed in the same manner as in Synthesis Example 6, except that 0.205 g of tri-n-butylphosphine oxide was used instead of using 0.409 g of tri-n-butylphosphine oxide.

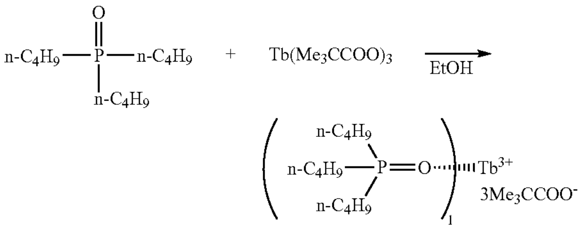

The characteristic absorption of P═O in the FTIR spectrum for the complex obtained was at 1133 $cm^{-1}$.

Synthesis Example 11

<Synthesis of Complex of Terbium Pivalate and Tri-n-Butylphosphine Oxide (TbPv-NBPO-3)>

Synthesis was performed in the same manner as in Synthesis Example 6, except that 0.614 g of tri-n-butylphosphine oxide was used instead of using 0.409 g of tri-n-butylphosphine oxide.

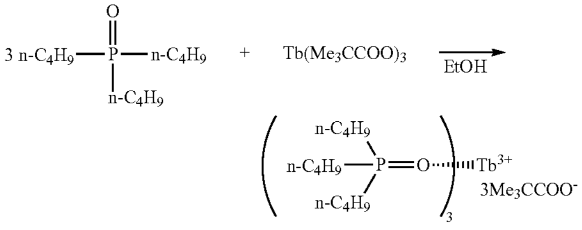

The characteristic absorption of P═O in the FTIR spectrum for the complex obtained was at 1132 $cm^{-1}$.

Synthesis Example 12

<Synthesis of Complex of Terbium Pivalate and Di-n-Butyl Sulfoxide (Tb-1)>

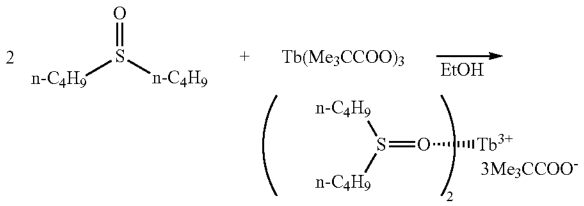

In 30 mL of methanol, 0.3 g of terbium pivalate obtained in Synthesis Example 1 and 0.409 g of di-n-butyl sulfoxide were dissolved, and the resultant was heated to reflux for 4 hours. After allowing to cool, methanol was distilled off under reduced pressure, 30 mL of diethyl ether was added to the residue, unreacted terbium pivalate precipitated was removed through filtration, and the filtrate was concentrated and dried under reduced pressure to obtain 0.177 g of the target complex of terbium pivalate and di-n-butyl sulfoxide.

Synthesis Example 13

<Synthesis of Complex of Terbium Valerate and Di-n-Butyl Sulfoxide>

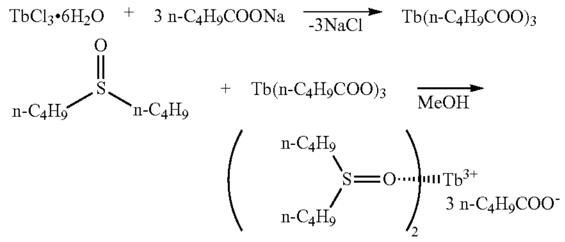

In 10 mL of water, 1 g of terbium chloride hexahydrate was dissolved, to which 0.997 g of sodium valerate dissolved in water was added, and the resultant was stirred at room temperature. Terbium pivalate precipitated was separated through filtration, washed with a small volume of water, and then dried under reduced pressure to obtain 0.93 g of terbium valerate. Subsequently, 0.3 g of terbium valerate and 0.211 g of di-n-butyl sulfoxide were dissolved in 30 mL of methanol, and the resultant was heated to reflux for 6 hours. The solvent was distilled off, diethyl ether was added, insoluble unreacted terbium valerate in a very small volume was removed through filtration, and the filtrate was concentrated and vacuum-dried to obtain 0.49 g of the target complex of terbium valerate and di-n-butyl sulfoxide.

Example 1

In 25 mL of DMSO, 26.7 mg of terbium pivalate (TbPv) obtained in Synthesis Example 1 was dissolved to prepare a TbPv solution (concentration: 1 mM). Subsequently, 13.5 mg of N-acetyl-L-tyrosine ethyl ester (Ac-Tyr-OEt) was dissolved in 50 mL of DMSO to prepare a solution of Ac-Tyr-OEt (concentration: 1 mM). Mixed were 2 mL of the TbPv solution and 2 mL of the Ac-Tyr-OEt solution, the mixture was left to stand at room temperature for 10 minutes, and a 3-mL portion of the resultant was then put in a quartz cell (b). In addition, 2 mL of the TbPv solution and 2 mL of DMSO were mixed, and, 10 minutes thereafter, a 3-mL portion of the mixture was put in a quartz cell (a). The two solutions obtained were irradiated with an LED at a wavelength of 300 nm to check the presence of fluorescence emission (FIG. 1). The results showed that almost no fluorescence emission was present in the DMSO solution (a) with TbPv alone, whereas the DMSO solution (b) with addition of Ac-Tyr-OEt having a tyrosine structure exhibited yellowish green fluorescence emission characteristic to a terbium complex, demonstrating that tyrosine structures can be sensed. Further, a DMSO solution (c) containing Ac-Tyr-OEt alone was irradiated with an LED at a wavelength of 300 nm to find that the DMSO solution (c) exhibited no fluorescence emission (FIG. 1).

Comparative Example 1

Figure 2:
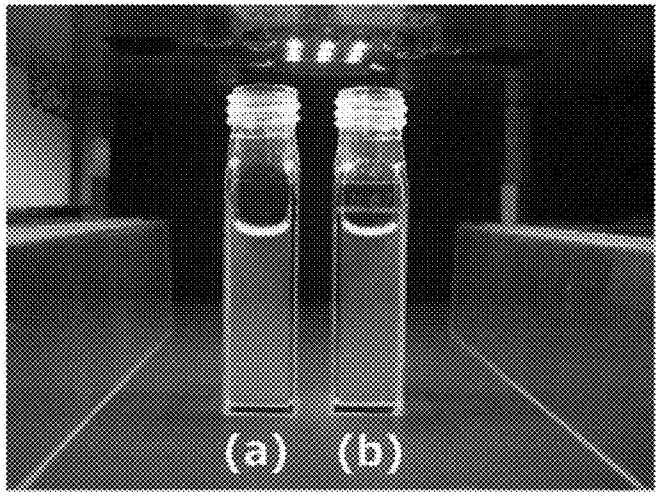
FIG. 2 shows a photograph for confirming fluorescence emission in Comparative Example 1, wherein (a) shows a result for a DMSO solution of TbPv and (b) shows a result for a DMSO solution of TbPv+N-acetyl-L-phenylalanine (Ac-Phe-OH)

In 25 mL of DMSO, 26.7 mg of terbium pivalate (TbPv) obtained in Synthesis Example 1 was dissolved to prepare a TbPv solution. Subsequently, 5.18 mg of N-acetyl-L-phenylalanine (Ac-Phe-OH) was dissolved in 25 mL of DMSO to prepare a solution of Ac-Phe-OH (concentration: 1 mM). Mixed were 2 mL of the TbPv solution and 2 mL of the Ac-Phe-OH solution, the mixture was left to stand at room temperature for 10 minutes, and a 3-mL portion of the resultant was then put in a quartz cell (b). In addition, 2 mL of the TbPv solution and 2 mL of DMSO were mixed, and, 10 minutes thereafter, a 3-mL portion of the mixture was put in a quartz cell (a). The two solutions obtained were irradiated with an LED at a wavelength of 300 nm to check the presence of fluorescence emission (FIG. 2). The results revealed that TbPv does not react with a phenylalanine structure, one of amino acids, and exhibits no fluorescence emission.

The results of Example 1 and Comparative Example 1 demonstrated that terbium pivalate can selectively detect tyrosine structures (tyrosine residues).

Example 2

<Fluorescence Spectrometry>

Figure 3:
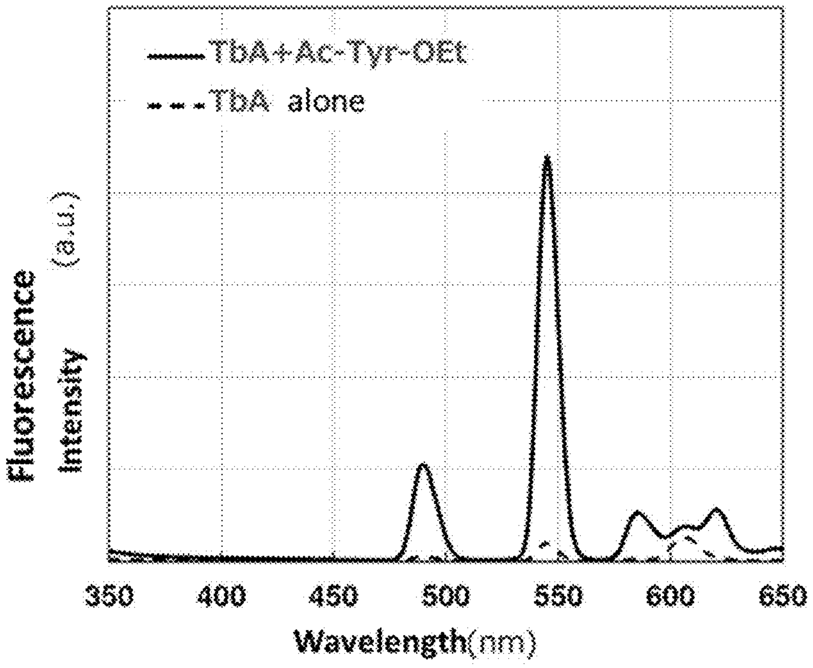
FIG. 3 shows fluorescence spectrum curves obtained through measurement in Example 2.

A DMSO solution of terbium(III) acetate tetrahydrate (TbA) (concentration: 1.5 mM) was prepared. In addition, a DMSO solution of N-acetyl-L-tyrosine ethyl ester (Ac-Tyr-OEt) (concentration: 4.5 mM) was prepared. Subsequently, 3 mL of the DMSO solution of TbA and 1 mL of the DMSO solution of Ac-Tyr-OEt were mixed, the mixture was left to stand for 10 minutes and then put in a quartz cell, and a fluorescence spectrum was determined at an excitation wavelength of 303 nm (TbA+Ac-Tyr-OEt). In addition, 3 mL of the TbA solution and 1 mL of DMSO were mixed, the mixture was left to stand for 10 minutes and then put in a quartz cell, and a fluorescence spectrum was determined at an excitation wavelength of 303 nm (TbA alone). FIG. 3 shows the fluorescence spectrum curves obtained. The solid line represents the fluorescence spectrum for the solution with addition of Ac-Tyr-OEt to TbA, and the dashed line represents the fluorescence spectrum for TbA alone. These results revealed that TbA itself emits almost no fluorescence but exhibits fluorescence emission characteristic to terbium (maximum wavelength: 545 nm) through reaction with Ac-Tyr-OEt.

Example 3

<Influence of Counteranion of Terbium Compound>

A DMSO solution of terbium pivalate (TbPv) obtained in Synthesis Example 1 (concentration: 1.5 mM) was prepared. In addition, a DMSO solution of N-acetyl-L-tyrosine ethyl ester (Ac-Tyr-OEt) (concentration: 4.5 mM) was prepared. Subsequently, 3 mL of the TbPv solution and 1 mL of the Ac-Tyr-OEt solution were mixed, the mixture was left to stand for 10 minutes and then put in a quartz cell, and a fluorescence spectrum was determined at an excitation wavelength of 303 nm (TbPv+Ac-Tyr-OEt). In addition, 3 mL of the TbPv solution and 1 mL of DMSO were mixed, the mixture was left to stand for 10 minutes and then put in a quartz cell, and a fluorescence spectrum was determined at an excitation wavelength of 303 nm (TbPv alone). For each of the fluorescence spectra, fluorescence intensity at a wavelength of 545 nm was measured, and the ratio (fluorescence intensity of TbPv+Ac-Tyr-OEt/fluorescence intensity of TbPv alone, hereinafter referred to as "sensitivity") was calculated. From the result, the sensitivity was determined to be 80.

Examples 4 to 12, Comparative Examples 2, 3

Sensitivity was calculated from fluorescence spectra in the same manner as in Example 3, except that terbium compounds listed in Table 5 were used in place of terbium pivalate. Similarly, for the cases with use of terbium chloride hexahydrate or terbium nitrate hexahydrate, as Comparative Examples, fluorescence spectra were determined and sensitivity was calculated. Table 5 shows the results obtained. These results found that the reaction of a terbium compound whose counteranion was chloride ion or nitrate ion and the tyrosine derivative gave sensitivity as low as 4 to 5, but that the terbium compound of the present invention whose counteranion was carboxylate ion (Y—$COO^-$) gave high sensitivity, demonstrating the effectiveness for detection of tyrosine structures.

TABLE 5

| Example | Terbium compound | Sensitivity (fluorescence intensity ratio at a wavelength of 545 nm) |
|---|---|---|
| Example 3 | Terbium compound obtained in Synthesis Example 1 | 80 |
| Example 4 | Terbium compound obtained in Synthesis Example 2 | 28 |
| Example 5 | Terbium compound obtained in Synthesis Example 3 | 27 |
| Example 6 | Terbium compound obtained in Synthesis Example 4 | 29 |
| Example 7 | Terbium compound obtained in Synthesis Example 5 | 87 |
| Example 8 | Terbium compound obtained in Synthesis Example 6 | 51 |
| Example 9 | Terbium compound obtained in Synthesis Example 9 | 30 |
| Example 10 | Terbium compound obtained in Synthesis Example 10 | 33 |
| Example 11 | Terbium compound obtained in Synthesis Example 11 | 34 |
| Example 12 | Terbium compound obtained in Synthesis Example 13 | 29 |
| Comparative Example 2 | Terbium chloride hexahydrate | 4 |
| Comparative Example 3 | terbium nitrate hexahydrate | 5 |

Comparative Examples 4 to 9

<Evaluation of Selectivity for Amino Acid Structure>

Figure 4:
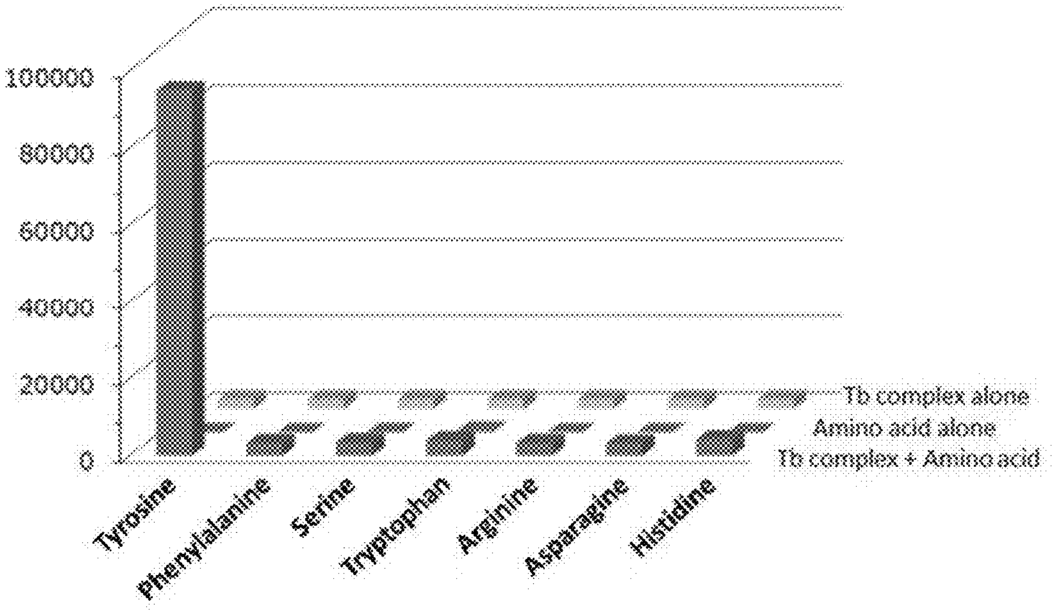
FIG. 4 shows a graph representing comparison of fluorescence intensities measured in Example 2 and Comparative Examples 4 to 9.

In the same manner as in Example 2, except that different amino acids shown in Table 6 were used in place of N-acetyl-L-tyro sine ethyl ester (Ac-Tyr-OEt), fluorescence spectra were determined after mixing with the TbA solution. Table 6 shows amino acid residues contained in different amino acid derivatives, and fluorescence intensity (arbitrary unit (a.u.)) at a wavelength of 545 nm for mixed solutions of an amino acid derivative and TbA (Amino acid+TbA), solutions of an amino acid derivative alone (Amino acid alone), and solutions of TbA alone (TbA alone). FIG. 4 is a graph generated from them, wherein the abscissa represents amino acid residues, and the ordinate represents fluorescence intensity (arbitrary unit (a.u.)) at a wavelength of 545 nm.

TABLE 6

| | | | Fluorescence intensity (arbitrary unit) | | |
|---|---|---|---|---|---|
| | Amino acid derivative | Amino acid residue | Amino acid+ TbA | Amino acid alone | TbA alone |
| Example 2 | N-acetyl-L-tyrosine ethyl ester (Ac-Tyr-OEt) | Tyrosine | 95012 | 65 | 2493 |
| Comparative Example 4 | N-acetyl-L-phenylalanine (Ac-Phe-OH) | Phenylalanine | 3259 | 36 | 2494 |
| Comparative Example 5 | N-(tert-butoxycarbonyl)-L-serine methyl (BOC-Ser-OEt) | Serine | 3463 | 52 | 2495 |
| Comparative Example 6 | N-acetyl-L-tryptophan ethyl (Ac-Trp-OEt) | Tryptophan | 3943 | 430 | 2496 |
| Comparative Example 7 | N2-acetyl-L-arginine (Ac-Arg-OH) | Arginine | 3279 | 3 | 2497 |
| Comparative Example 8 | Nα-(t-butoxycarbonyl)-L-asparagine (tBOC-Asn-OEt) | Asparagine | 3171 | 11 | 2498 |
| Comparative Example 9 | N-acetyl-L-histidine (Ac-His-OH) | Histidine | 4212 | 22 | 2499 |

Comparison between Example 2 and Comparative Examples 4 to 9 demonstrated that TbA can selectively detect tyrosine structures.

Example 13

Figure 5:
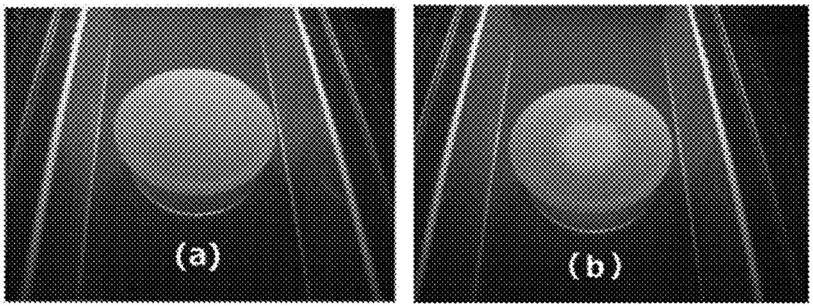
FIG. 5 shows photographs for confirming fluorescence emission in Example 13, wherein (a) shows a result of confirming fluorescence emission for a piece of filter paper with dropping a DMSO solution of terbium acetate tetrahydrate (TbA) and subsequent drying, and (b) shows a result of confirming fluorescence emission for a piece of filter paper with dropping a DMSO solution of TbA, subsequent drying, and dropping a DMSO solution of Ac-Tyr-OEt.

A DMSO solution of terbium acetate (concentration: 30 mM) was prepared, and 0.2 mL of the resulting solution was dropped onto each of two circular pieces of filter paper (40 mmϕ), and the pieces of filter paper were dried at 60° C. Subsequently, 0.03 mL of an ethanol solution of N-acetyl-L-tyrosine ethyl ester (Ac-Tyr-OEt) (concentration: 1 mM) was dropped on one of the pieces of filter paper, and the piece of filter paper was dried at room temperature. The piece of filter paper after that was irradiated with an LED at a wavelength of 303 nm to observe fluorescence emission. The results showed that, as shown in FIG. 5, no fluorescence emission was found in the piece of filter paper (a) without dropping the Ac-Tyr-OEt solution, whereas green fluorescence emission characteristic to a terbium complex was confirmed in the piece of filter paper (b) with dropping the Ac-Tyr-OEt solution, demonstrating that detection in solid media can be performed.

Example 14

<Detection of Peptide Oligomer—1>

Figure 6:
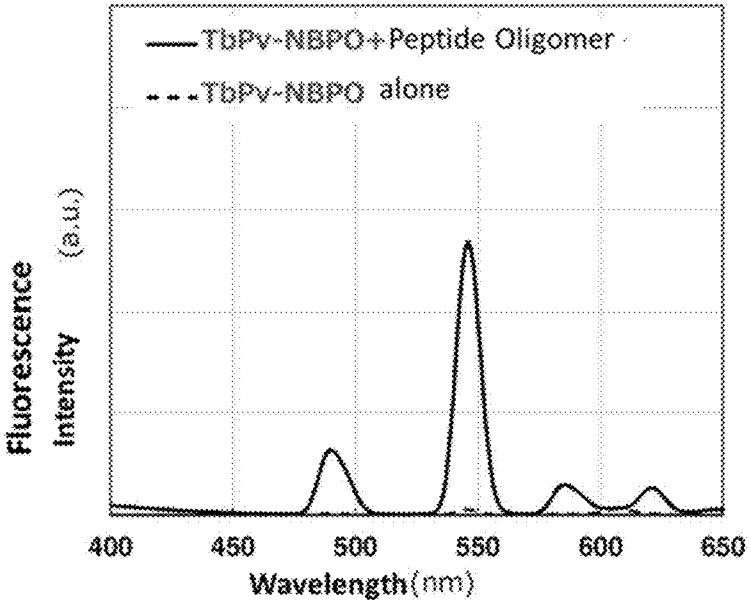
FIG. 6 shows fluorescence spectrum curves obtained through measurement in Example 14.

A DMSO solution of the terbium compound obtained in Synthesis Example 6 (TbPv-NBPO) was prepared (concentration: 1.5 mM). A DMSO solution of a peptide oligomer (N-acetylleucine-glutamine-serine-tyrosine methyl ester: Ac-Leu-Gln-Ser-Tyr-OMe) was prepared (concentration: 4.5 mM). Mixed were 3 mL of the TbPv-NBPO solution and 1 mL of the Ac-Leu-Gln-Ser-Tyr-OMe solution, and the mixture was left to stand at room temperature for 10 minutes. Thereafter, 3 mL of the mixed solution was put in a quartz cell, and a fluorescence spectrum was determined. 3 mL of the TbPv-NBPO solution and 1 mL of DMSO were mixed, and the mixture was left to stand at room temperature for 10 minutes. Thereafter, 3 mL of the mixed solution was put in a quartz cell, and a fluorescence spectrum was determined. FIG. 6 shows the fluorescence spectra obtained. From TbPv-NBPO+peptide oligomer (solid line), intense fluorescence at a wavelength of 545 nm, which is characteristic to a Tb complex, was found. By contrast, TbPv-NBPO alone (dashed line) was found to exhibit very weak fluorescence emission. These results demonstrated that TbPv-NBPO can even detect peptide oligomers containing a tyrosine structure.

Example 15

<Detection of Peptide Oligomer—2>

Figure 7:
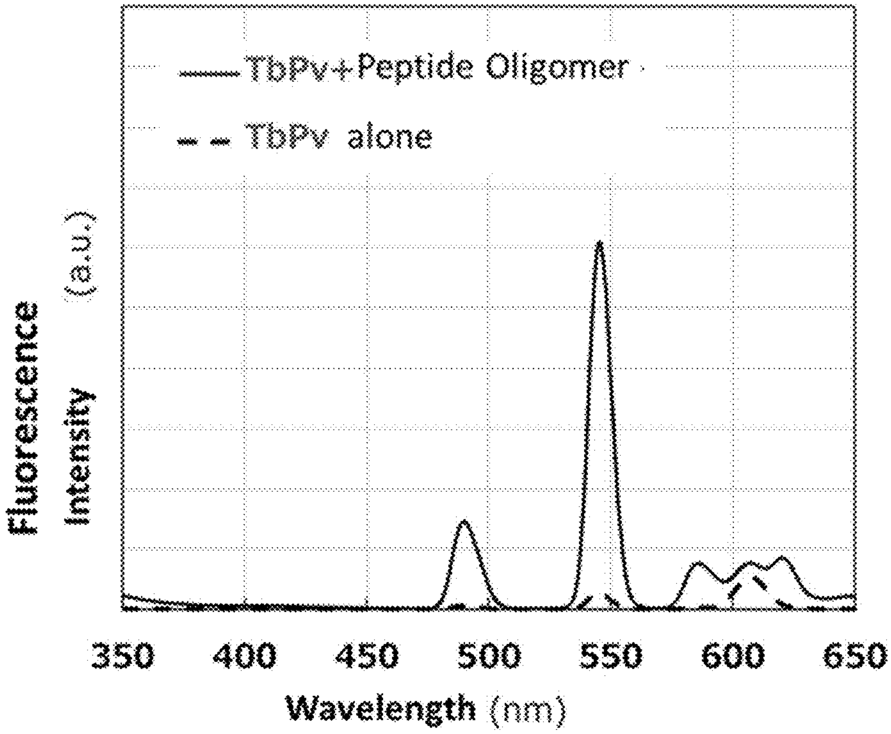
FIG. 7 shows fluorescence spectrum curves obtained through measurement in Example 15.

A DMSO solution of terbium pivalate (TbPv) obtained in Synthesis Example 1 was prepared (concentration: 1.7 mM). In addition, a DMSO solution of a peptide oligomer (glycine-glycine-tyrosine-arginine: Gly-Gly-Tyr-Arg) was prepared (concentration: 4.5 mM). Mixed were 3 mL of the TbPv solution and 1 mL of the Gly-Gly-Tyr-Arg solution, and the mixture was left to stand at room temperature for 10 minutes. Thereafter, 3 mL of the mixed solution was put in a quartz cell, and a fluorescence spectrum was determined. In addition, 3 mL of the TbPv solution and 1 mL of DMSO were mixed, and the mixture was left to stand at room temperature for 10 minutes. Thereafter, 3 mL of the mixed solution was put in a quartz cell, and a fluorescence spectrum was determined. FIG. 7 shows the fluorescence spectra obtained. From TbPv+peptide oligomer (solid line), intense fluorescence at a wavelength of 545 nm, which is characteristic to a Tb complex, was found. By contrast, TbPv alone (dashed line) was found to exhibit very weak fluorescence emission. These results demonstrated that TbPv can even detect peptide oligomers containing a tyrosine structure.

Example 16

Figure 8:
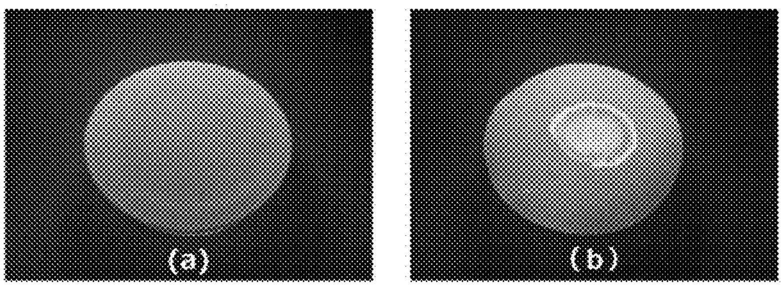
FIG. 8 shows photographs for confirming fluorescence emission in Example 16.

A DMSO solution of terbium pivalate obtained in Synthesis Example 1 and 1-ethyl-3-methylimidazolium acetate were mixed at a volume ratio of 4:1 to prepare a solution (concentration of terbium pivalate: 50 mM). 0.2 mL of the resulting solution was dropped onto each of two circular pieces of filter paper (40 mmΦ), and the pieces of filter paper were dried at 60° C. Subsequently, 0.03 mL of HEPES (2-[4-(2-hydroxyethyl)-1-piperazinyl]ethanesulfonic acid) buffered aqueous solution of N-acetyl-L-tyrosine ethyl ester (Ac-Tyr-OEt) (concentration: 50 mM, pH=7.7, adjusted with NaOH aqueous solution) was dropped on one of the pieces of filter paper, and the piece of filter paper was dried at 60° C. The obtained filter papers were irradiated with an LED at a wavelength of 303 nm to observe fluorescence emission. The results showed that, as shown in FIG. 8, no fluorescence emission was found in the filter paper (a) without dropping the Ac-Tyr-OEt solution, whereas green fluorescence emission characteristic to a terbium complex was confirmed in the piece of filter paper (b) with dropping the Ac-Tyr-OEt solution, demonstrating that detection even using an aqueous solution containing a tyrosine residue can be performed.

Example 17

Figure 9:
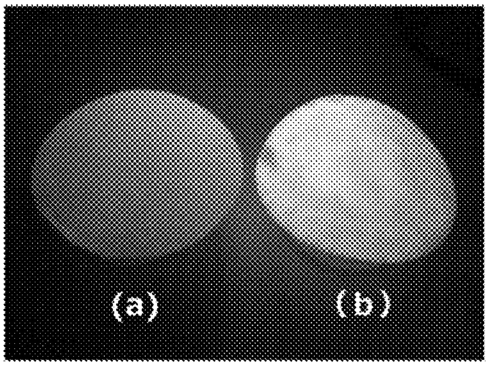
FIG. 9 shows photographs for confirming fluorescence emission in Example 17.
Figure 10:
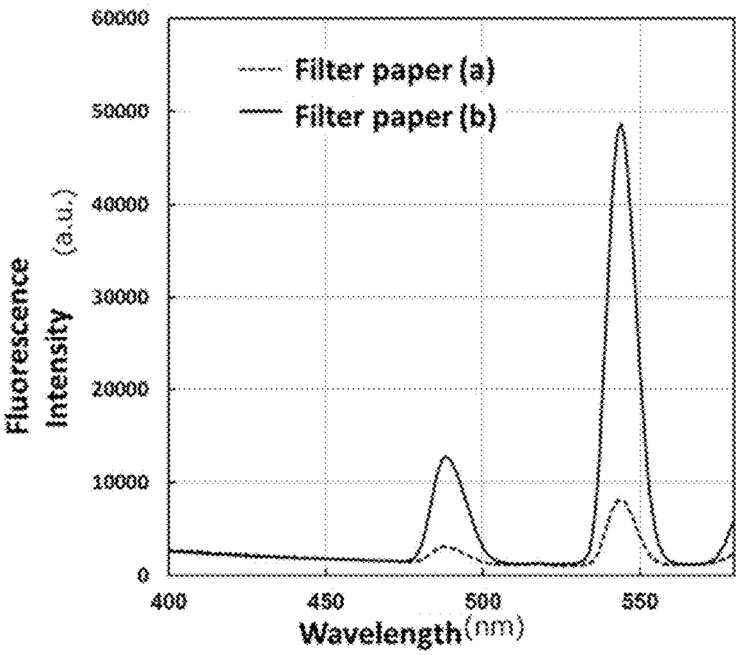
FIG. 10 shows fluorescence spectrum curves obtained through measurement in Example 17.

A DMSO solution of a complex of terbium pivalate and tri-n-butylphosphine oxide (TbPv-NBPO) obtained in Synthesis Example 6 and 1-ethyl-3-methylimidazolium acetate were mixed at a volume ratio of 4:1 to prepare a solution (concentration of TbPv-NBPO: 50 mM). 0.2 mL of the resulting solution was dropped onto each of two circular pieces of filter papers (40 mmD), and the pieces of filter paper were dried at 60° C. Subsequently, 0.15 mL of HEPES (2-[4-(2-hydroxyethyl)-1-piperazinyl]ethanesulfonic acid) buffered aqueous solution of N-acetyl-L-tyrosine ethyl ester (Ac-Tyr-OEt) (concentration: 25 mM, pH=7.7, adjusted with NaOH aqueous solution) was dropped on one of the pieces of filter paper, and the piece of filter paper was dried at 60° C. The obtained filter papers were irradiated with an LED at a wavelength of 303 nm to observe fluorescence emission. The results showed that, as shown in FIG. 9, no fluorescence emission was found in the filter paper (a) without dropping the Ac-Tyr-OEt solution, whereas green fluorescence emission characteristic to a terbium complex was confirmed in the piece of filter paper (b) with dropping the Ac-Tyr-OEt solution. The fluorescence spectra (excitation wavelength: 303 nm) of the filter paper (a) and filter paper (b) were also measured. As a result, as shown in FIG. 10, it was found that the fluorescence intensity at a wavelength of 544 nm, which is characteristic to a terbium complex, was large in the filter paper (b) with dropping the Ac-Tyr-OEt solution as compared to that in the filter paper (a) without dropping the Ac-Tyr-OEt solution.

Example 18

Figure 11:
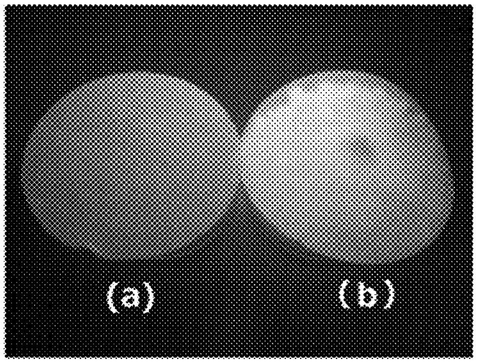
FIG. 11 shows photographs for confirming fluorescence emission in Example 18.
Figure 12:
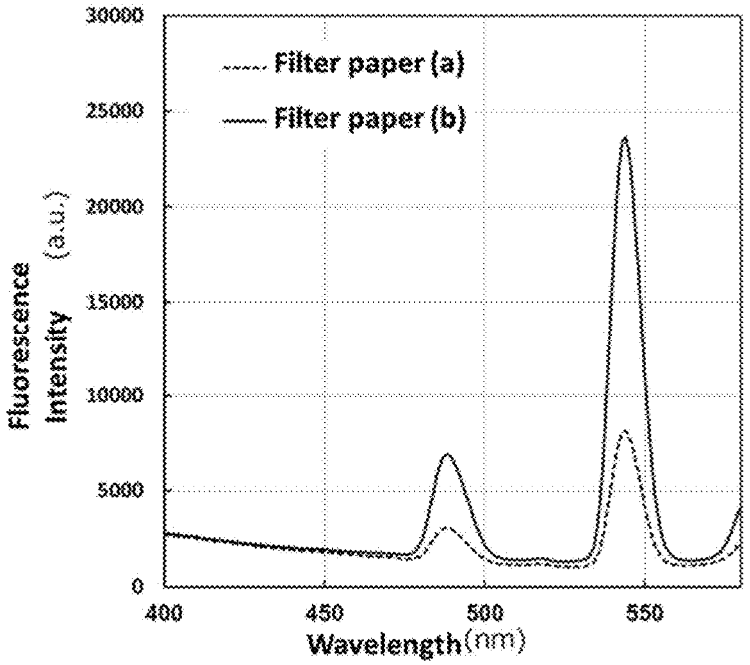
FIG. 12 shows fluorescence spectrum curves obtained through measurement in Example 18.

A DMSO solution of a complex of terbium pivalate and tri-n-butylphosphine oxide (TbPv-NBPO) obtained in Synthesis Example 6 and 1-ethyl-3-methylimidazolium acetate were mixed at a volume ratio of 4:1 to prepare a solution (concentration of TbPv-NBPO: 50 mM). 0.2 mL of the resulting solution was dropped onto each of two circular pieces of filter papers (40 mm(D), and the pieces of filter paper were dried at 60° C. Subsequently, 0.15 mL of HEPES (2-[4-(2-hydroxyethyl)-1-piperazinyl]ethanesulfonic acid) buffered aqueous solution of N-acetyl-L-tyrosine ethyl ester (Ac-Tyr-OEt) (concentration: 5 mM, pH=7.7, adjusted with NaOH aqueous solution) was dropped on one of the pieces of filter paper, and the piece of filter paper was dried at 60° C. The obtained filter papers were irradiated with an LED at a wavelength of 303 nm to observe fluorescence emission. The results showed that, as shown in FIG. 11, no fluorescence emission was found in the filter paper (a) without dropping the Ac-Tyr-OEt solution, whereas green fluorescence emission characteristic to a terbium complex was confirmed in the piece of filter paper (b) with dropping the Ac-Tyr-OEt solution. The fluorescence spectra (excitation wavelength: 303 nm) of the filter paper (a) and filter paper (b) were also measured. As a result, as shown in FIG. 12, it was found that the fluorescence intensity at a wavelength of 544 nm, which is characteristic to the terbium complex, was large in the filter paper (b) with dropping the Ac-Tyr-OEt solution as compared to that in the filter paper (a) without dropping the Ac-Tyr-OEt solution.

While the invention has been described with reference to example embodiments and examples thereof, the invention is not limited to these embodiments and examples. Various changes that can be understood by those of ordinary skill in the art may be made to form and details of the present invention without departing from the spirit and scope of the present invention.

The whole or part of the example embodiments disclosed above can be described as, but not limited to, the following supplementary notes.

(Supplementary Note 1)

A method for (preferably selectively) detecting a tyrosine residue in a sample, wherein fluorescence emission from a reaction product of a terbium compound and a tyrosine residue is detected, the terbium compound being represented by the following formula (1):

(1)

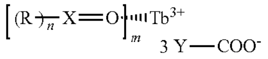

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same X atom or different X atoms are optionally attached to each other; X represents phosphorus atom or sulfur atom; Y represents hydrocarbon group having 1 to 12 carbon atoms; n represents an integer of 1 to 3 and m represents an integer of 0 to 5; and, if m is 2 or more, X atoms are identical to or different from each other.

(Supplementary Note 2)

The method according to Supplementary note 1, wherein fluorescence emitted from a complex of terbium formed through reaction of a tyrosine residue and the terbium compound is detected.

(Supplementary Note 3)

A fluorescence-labeling reagent for (preferably selectively) detecting a tyrosine residue, wherein the fluorescence-labeling reagent comprises a terbium compound represented by the following formula (1):

(1)

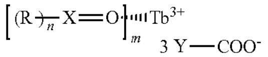

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same X atom or different X atoms are optionally attached to each other; X represents phosphorus atom or sulfur atom; Y represents hydrocarbon group having 1 to 12 carbon atoms; n represents an integer of 1 to 3 and m represents an integer of 0 to 5; and, if m is 2 or more, X atoms are identical to or different from each other.

(Supplementary Note 4)

A terbium compound represented by the following formula (2):

(2)

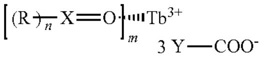

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same X atom or different X atoms are optionally attached to each other; X represents phosphorus atom or sulfur atom; Y represents hydrocarbon group having 1 to 12 carbon atoms; n represents an integer of 1 to 3 and m represents an integer of 1 to 5; and, if m is 2 or more, X atoms are identical to or different from each other.

(Supplementary Note 5)

A terbium compound represented by the following formula (3):

(3)

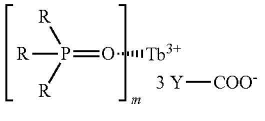

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same P atom or different P atoms are optionally attached to each other; Y represents hydrocarbon group having 1 to 12 carbon atoms; and m represents an integer of 1 to 5.

(Supplementary Note 6)

A terbium compound represented by the following formula (4):

(4)

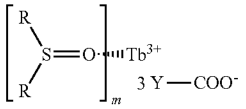

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same S atom or different S atoms are optionally attached to each other; Y represents hydrocarbon group having 1 to 12 carbon atoms; and m represents an integer of 1 to 5.

(Supplementary Note 7)

The method according to Supplementary note 1, comprising the steps of:

(i) reacting the terbium compound represented by the formula (1) and a sample to obtain a reaction product;

(ii) irradiating the resulting reaction product with excitation light; and (iii) detecting excited fluorescence.

(Supplementary Note 8)

A sensor for (preferably selectively) detecting a tyrosine residue, the sensor comprising a detection section configured to detect fluorescence emission from a reaction product of a terbium compound and a tyrosine residue, the terbium compound being represented by the following formula (1):

(1)

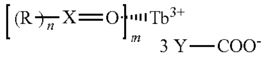

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same X atom or different X atoms are optionally attached to each other; X represents phosphorus atom or sulfur atom; Y represents hydrocarbon group having 1 to 12 carbon atoms; n represents an integer of 1 to 3 and m represents an integer of 0 to 5; and, if m is 2 or more, X atoms are identical to or different from each other.

(Supplementary Note 9)

The fluorescence-labeling reagent according to Supplementary note 3, further comprising at least one ionic liquid selected from the group consisting of an imidazolium salt, a phosphonium salt, a pyridinium salts, an ammonium salt, a piperidinium salt, and a pyrrolidinium salt.

(Supplementary Note 10)

The fluorescence-labeling reagent according to Supplementary note 9, wherein the ionic liquid is at least one compound selected from the group consisting of 1-ethyl-3-methylimidazolium acetate, 1-butyl-3-methylimidazolium acetate, 1-ethyl-3-methylimidazolium tetrafluoroborate, 1-butyl-1-methylpyrrolidinium bis(fluorosulfonyl)imide, 1-butylpyridinium bis(trifluoromethanesulfonyl)imide, 1-methyl-1-propylpiperidinium bis(fluorosulfonyl)imide, 1-ethyl-3-methylimidazolium bis(trifluoromethanesulfonyl) imide, and 1-butyl-3-methylimidazolium dicyanamide.

(Supplementary Note 11)

A method for determining a concentration of a tyrosine residue in a sample, comprising measuring an intensity of fluorescence emission from a reaction product of a terbium compound and a tyrosine residue is measured, the terbium compound being represented by the following formula (1):

(1)

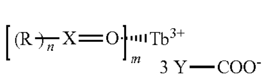

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same X atom or different X atoms are optionally attached to each other; X represents phosphorus atom or sulfur atom; Y represents hydrocarbon group having 1 to 12 carbon atoms; n represents an integer of 1 to 3 and m represents an integer of 0 to 5; and, if m is 2 or more, X atoms are identical to or different from each other.

INDUSTRIAL APPLICABILITY

By using the terbium compound having the specific structure of the present embodiment, a tyrosine residue in a sample can be (preferably selectively) detected.

The invention claimed is:

1. A method for detecting a tyrosine residue in a sample, comprising detecting fluorescence emission from a reaction product of a terbium compound and a tyrosine residue, the terbium compound being represented by the following formula (1):

(1)

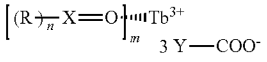

wherein R groups each independently represent alkyl group having 1 to 8 carbon atoms, alkenyl group having 2 to 8 carbon atoms, cycloalkyl group having 3 to 8 carbon atoms, or substituted or unsubstituted aryl group; R groups attached to the same X atom or different X atoms are optionally attached to each other; X represents phosphorus atom or sulfur atom; Y represents an alkyl group having 1 to 12 carbon atoms, a cycloalkyl group having 3 to 12 carbon atoms, or a phenyl group; n represents an integer of 1 to 3 and m represents an integer of 0 to 5; and, if m is 2 or more, X atoms may be identical to or different from each other.

2. The method according to claim 1, wherein fluorescence emitted from a complex of terbium formed through reaction of a tyrosine residue and the terbium compound is detected.

3. The method according to claim 1, comprising:

(i) reacting the terbium compound represented by the formula (1) and a sample to obtain a reaction product;

(ii) irradiating the resulting reaction product with excitation light; and (iii) detecting excited fluorescence.

4. The method according to claim 1, wherein the Y—$COO^-$ in formula (1) is at least one carboxylate ion selected from the group consisting of acetate ion, propanoate ion, pivalate ion, isobutyrate ion, cyclohexanecarboxylate ion, cyclopentanecarboxylate ion, and benzoate ion.

5. The method according to claim 1, wherein the Y—$COO^-$ in formula (1) is at least one carboxylate ion selected from the group consisting of acetate ion, propanoate ion, pivalate ion, isobutyrate ion, cyclohexanecarboxylate ion, and cyclopentanecarboxylate ion.

6. The method according to claim 1, wherein the tyrosine residue is selectively detected.

* * * * *